US00PP18335P3

(12) United States Plant Patent
Fortune

(10) Patent No.: US PP18,335 P3
(45) Date of Patent: Dec. 18, 2007

(54) ***SYZYGIUM AUSTRALE* PLANT NAMED '4TUNE8ONE'**

(50) Latin Name: *Syzygium australe*
Varietal Denomination: 4tune8one

(76) Inventor: Graham Fortune, Po Box 840, Cooroy, 4563, Queensland (AU)

( * ) Notice: Subject to any disclaimer, the term of this patent is extended or adjusted under 35 U.S.C. 154(b) by 0 days.

(21) Appl. No.: 11/367,121

(22) Filed: Mar. 3, 2006

(65) Prior Publication Data

US 2007/0209094 P1 Sep. 6, 2007

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
*Assistant Examiner*—June Hwu
(74) *Attorney, Agent, or Firm*—Christie, Parker & Hale, LLP

(57) ABSTRACT

A new a distinct of *Syzygium australe,* which is a periclinal chimera arising from a spontaneous mutation (sport) in a stock plant of a standard green *Syzygium australe,* is described. This new variety comprises a unique variegated leaf color, vigorous growth and compact foliage habit making it suitable for hedging plants, topiary species and tub specimens in domestic, commercial and recreational settings.

6 Drawing Sheets

Figure 1:
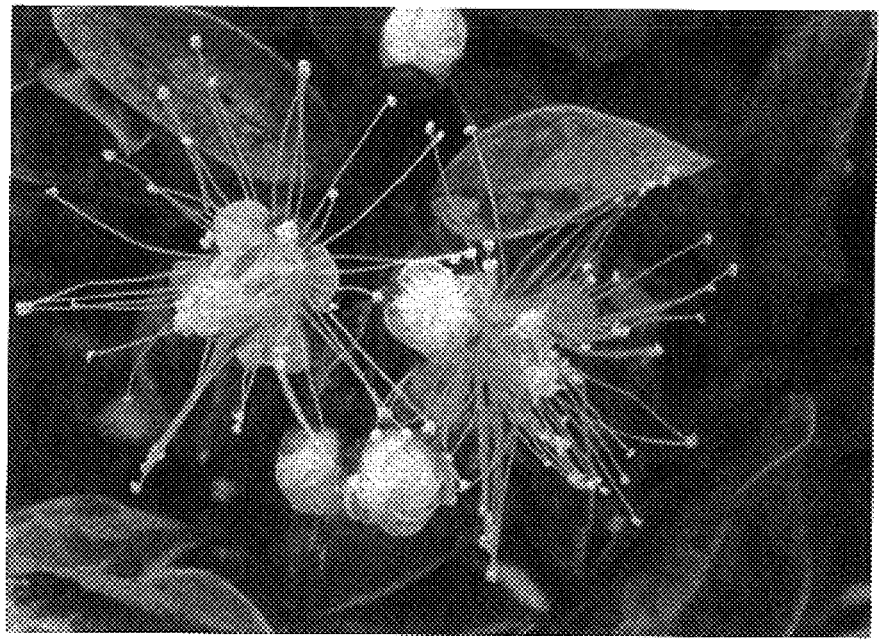

Botanical classification: *Syzygium australe.*
Cultivar denomination: '4Tume8one'.

BACKGROUND OF THE INVENTION

The present invention relates to a new and distinct variety of *Syzygium australe,* and herein after referred to by the varietal denomination of the new species '4tune8one'.

*Syzygium* is a genus of about 500 species occurring in tropical and subtropical rainforests. There are about 50 species in Australia occurring in the Kimberly region of Western Australia, the Northern Territory, Queensland and northern New South Wales. The species formerly known as *Eugenia australis* is now regarded as two separate species, *Syzygium australe* and *S.paniculatum.*

*S.australe* is a common plant of coastal and highland rainforests from southern New South Wales to central Queensland. In nature it can reach over 25 meters in height but is usually smaller in cultivation. The leaves are opposite (each pair emerges from the stem at the same location but on opposing sides), rounded and bright, glossy green in color. White flowers are followed by large, fleshy, red fruits in profusion. These are ovoid in shape and around 20 mm long with a large seed. The fruits are edibile and are often made into jams. They can also be eaten fresh and have a crisp, refreshing texture.

*S.australe* is a hardy tree in most temperature and subtropical climates and is cultivated in most Australian states. It prefers rich soils and assured moisture. At least two compact forms have been marked in recent years. These probably grow to no more than 2 meters and may be found under the names 'Blaze' and 'Tiny Trev'. The compact forms are suitable for growing in large containers.

There is an ongoing need worldwide, and in particular in the United States of America, for bushy, attractive, vigorous growing hedging plants, topiary species and tub specimens.

Such plants find use in domestic, commercial and recreational settings such as parks and gardens.

SUMMARY OF THE INVENTION

'4Tune8one' is a periclinal chimera resulting from a spontaneous mutation (sport) in a stock plant of a standard green *Syzygium australe* growing on the property of the inventor in Cooroy, Queensland, Australia. The new variety has been propagated vegetatively through six generations and have shown that the unique features of this new plant are stable and reproduced true to type.

COMPARISON WITH PARENTS AND COMPARABLE VARIETIES

The most similar variety known to the inventor is the variety 'Pearly Showers', the subject of U.S. Plant Pat. No. 5,286, issued Sep. 25, 1984. '4tune8one' differs from 'Pearly Showers' in that leaves emerge all year round, have a different leaf color, abundant flower development and persistence, and edible seeded fruit.

The primary features of this new variety which are distinctive over existing types comprise its variegated leaf color, vigorous growth and compact foliage habit. New growth comprises a combination of red hues occurring where the green parts of the mature leaf will eventually be. As the leaves mature the coloration changes to a yellow and yellow-green along the edges, and variable tones of brown-green, yellow-green and green in the centre of the leaf. Leaves show varying degrees of speckled and dappled variegation. Vigorous growth of this new variety includes new leaves emerging all year round, and leaves may persist even when stems mature into branches. The compact foliage habit with a dense foliage crown is observed.

BRIEF DESCRIPTION OF THE ILLUSTRATIONS

The accompanying photographic illustrations show typical species of the new variety, in color as nearly true as it is reasonably possible to make in a color illustration of this character. Colors in the photograph may differ from the color values cited in the detailed botanical description below, which accurately describes the colors of the new plant species.

FIG. 1 comprises a close up view of flowers of '4tune8one'. Note the white petals and pink-red colored sepals and the unique variegation of each leaf.

Figure 2:
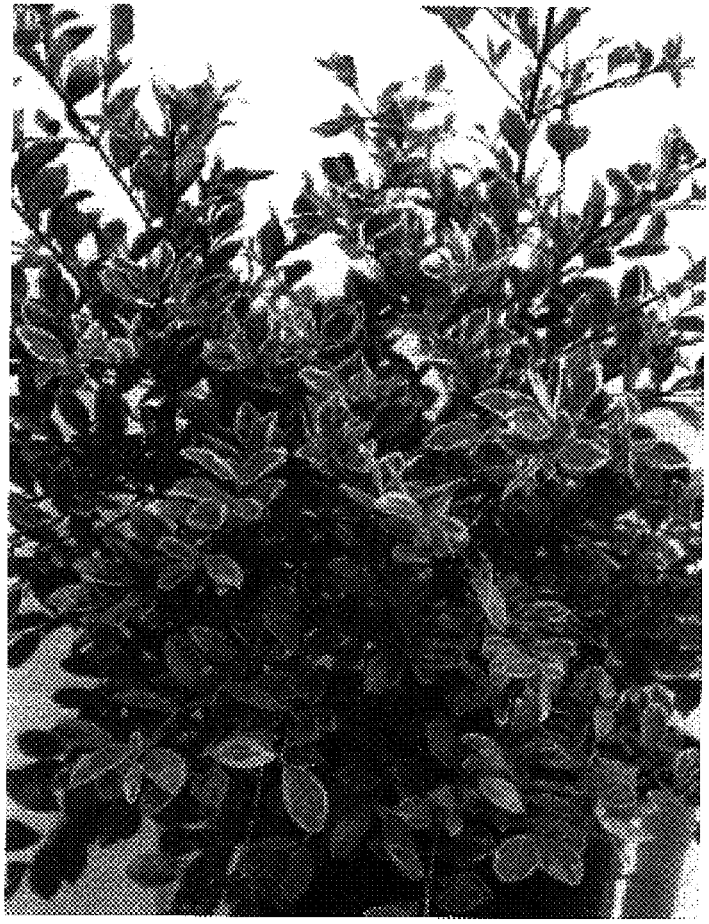

FIG. 2 comprises an overall view of variegated foliage on a 5-month-old plant.

Figure 3:
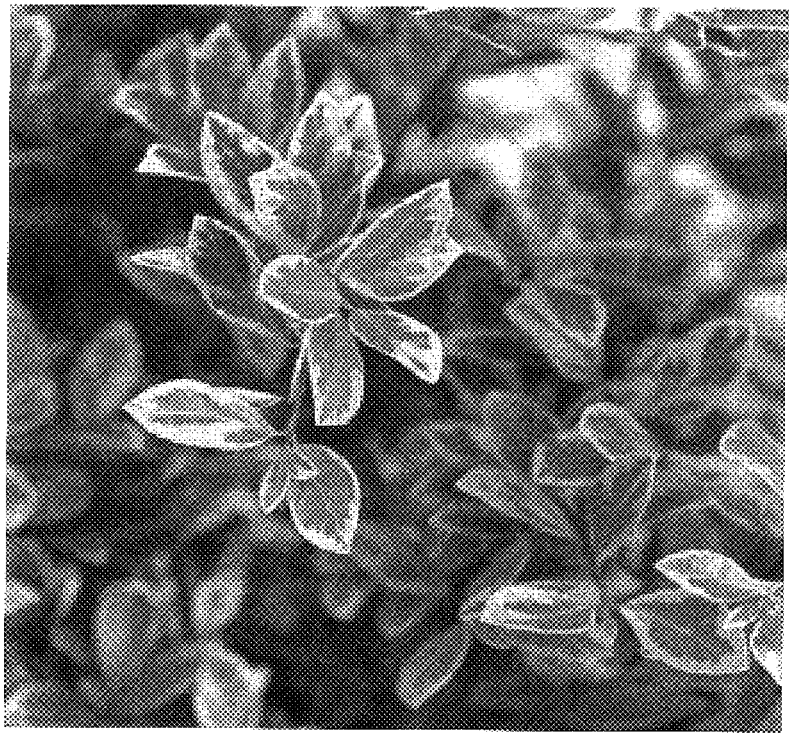

FIG. 3 comprises a close-up of mature variegated foliage.

Figure 4:
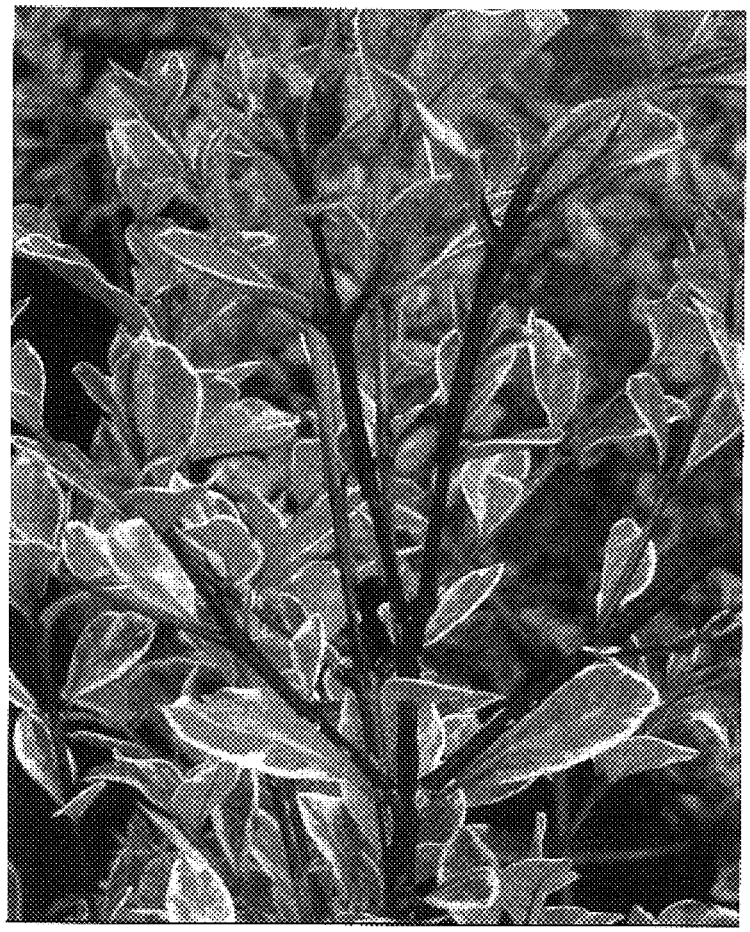

FIG. 4 comprises a view of the scarlet red new growth.

Figure 5:
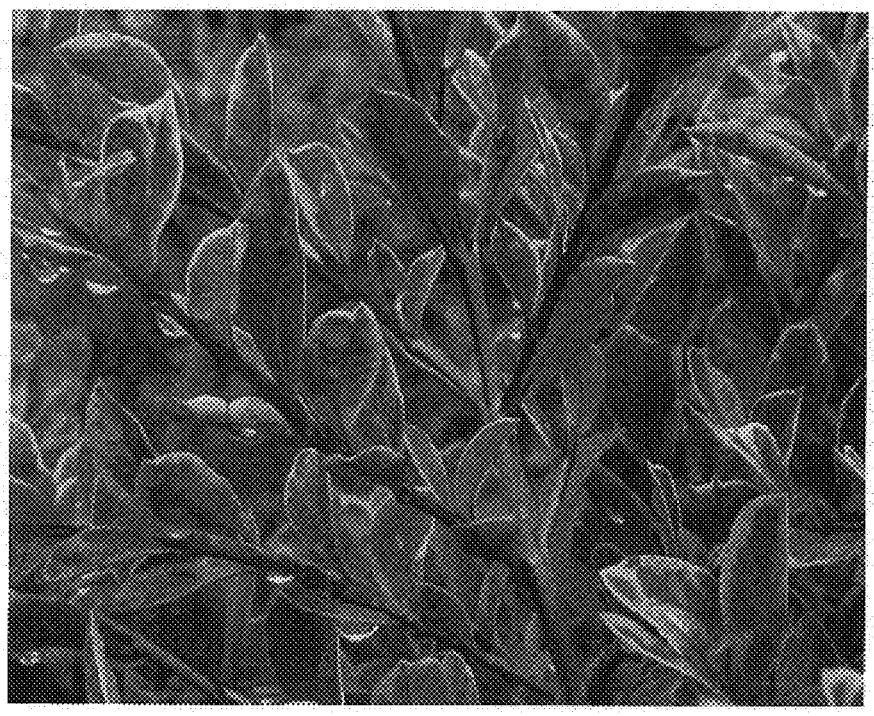

FIG. 5 comprises a view of the color change of the plant as stem matures.

Figure 6:
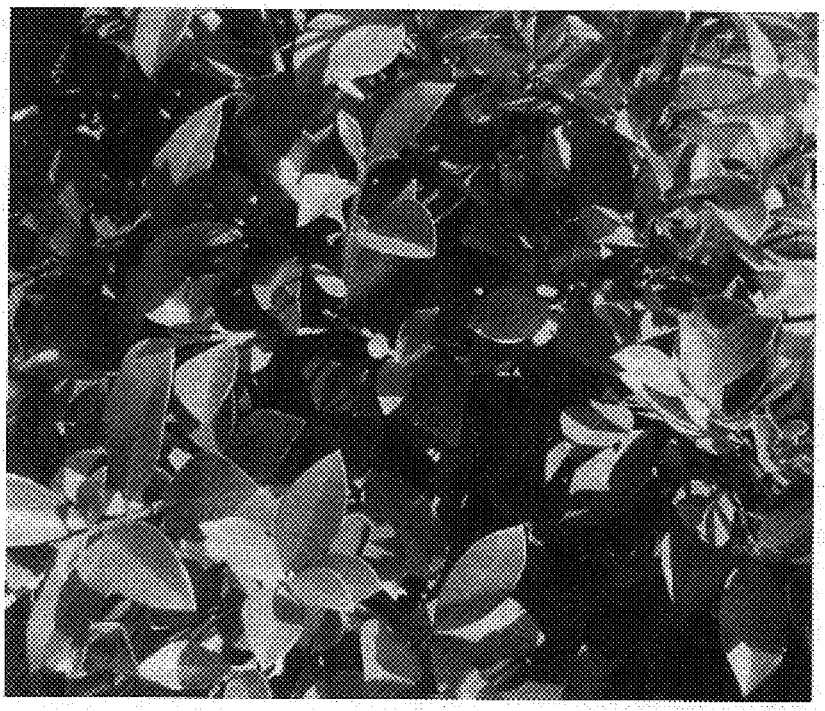

FIG. 6 comprises a view of a mother stock plant with normal green leaves.

DESCRIPTION OF THE NEW VARIETY

*Syzygium australe,* '4Tune8one' has not been observed under all possible environmental, cultural, and light conditions. The following observations and descriptions are of plants grown in containers at Cooroy, Queensland, Australia. Phenotypic expression may vary with light intensity, cultural, and environmental conditions. In this description, color is by reference to The Royal Horticultural Society chart (RHS) in respect of plants, for plants from 5 months to 2 years old.

Propagation:

The new variety developed from a natural sport of a *Syzygium australe* topiary at the nursery of the inventor, Graham Fortune in Cooroy, Queensland, Australia. The natural sport appeared in January 2003. Seven original sport cuttings were taken from the mother plant by the inventor and propagated on his property. The new variety is readily propagated, with 13,000 plants produced up to February 2006 on the inventor's property.

The new variety has been propagated vegetatively with 13,000 plants produced so far by vegetative propagation (asexual reproduction from stem cuttings). Only three off-types were observed amongst this group demonstrating extreme stability and uniformity.

The new variety is vegetatively propagated from root cuttings, stem sections or by tissue culture.

Plant description:

The new variety is a medium sized, vigorous, single or multi-trunked tree with a dense foliage crown. Ultimate height is unknown, but is presently 10 feet tall and 3 feet wide. It is probable that in cultivation this cultivar will reach a height of 23 feet and width of 5 feet. The non-variegated parent can reach an ultimate height of 70 feet.

Trunk description:

The trunk of '4tune8one' has a diameter of 0.65 inch when the tree is a height of 1 foot, 6 inches high and at a height of 6 feet tall the diameter of the trunk at ground level is 1.65 inches; when grown with a single trunk. The surface texture of the trunk is smooth with no discernable shedding bark. The texture of the trunk directly subtending a branch can have a slightly fissured appearance. The color of the trunk is a combination of RHS 198C, RHS 156C and RHS 199D.

Stem and branch description:

Stems and branches of '4tune8one' are disposed opposite each other, upright and 4-angled (0.16 inch×0.12 inch) and have a smooth texture when young. Internodes of the young stems range from 0.39 inch to 0.71 inch, increasing with age to a maximum internode length of 1.26 inches. The initial color of stems ranged from glossy orange-red RHS 44A through to glossy scarlet-red RHS 45B. The color darkens with age to dull orange-red RHS 53A as shown in FIGS. 4 and 5. Young stems have a longitudinal internodal scar/right in line with the base of the petiole where leaves are attached to the stem, they vary in color from red RHS 46A to bright red RHS 45C. The internodal scar/ridge are not visible after stems reach a diameter of 2.36 niches. As stems age and thicken the color changes to a dull yellow-green RHS 150C undertone with a greyed-yellow RHS 160C overtone. The mature stems and branches have a smooth texture with no discernible shedding bark. Branches will form from the main trunk/s from ground-level up.

Leaf description:

Leaves of '4-tune8one' are simple, shiny and shaped ovate to elliptic with young tips of leaves being acute. Mature leaves can be up to 1.7 inches long and 0.91 inch wide, with petioles being up to 0.24 inch long. The petioles are 4-angled (0.03 inch×0.03 inch) and have a smooth texture. The leaves have entire margins and are arranged in opposite decussate pairs. The upper surface texture of the leaf is smooth with the mid rib forming a slight depression along its entire length. The lower surface of the leaf is smooth with the mid rib being prominent and raised. Some mature leaves can have a crinkled appearance and texture, especially the variegated sections. Leaves are normally carried on 45° angles to the stem/branch. Leaves can be persistent even when stems mature into branches. New leaves emerge all year round, which is unusual for the species and compared to the cultivar Syzygium peniculatum 'Pearly Showers' U.S. Plant Pat. 5,286.

New foliage:

The new growth comprises one or a combination of the following red tones: RHS 53A, RHS 53B, RHS 47A, RHS 46B, RHS 45A, RHS 45B. These colors occur where the green part of the leaf will eventually be. The red pigmentations are especially vivid during cooler months.

Mature foliage:

The upper surface color of mature leaves is yellow-green RHS 153C, RHS153D, RHS 151A, RHS 151B, RHS 151C, RHS 151D, RHS 18C and RHS 11C along the edges and variable tones of color ranging from brown-green RHS 152B, yellow-green RHS 144A and green RHS 137A in the centre. All leaves show varying amounts of speckled and dappled variegation in each leaf. Some leaves can have up to 5 combinations of the above mentioned colors or can appear to only have two. Each leaf has a unique form of variegation as depicted in FIGS. 1–5. The lower surface color of mature leaves can be a combination of RHS 146A, RHS 151A and RHS 151C. The degree of variation and variegation is much more defined in the upper surface of the leaf. As leaves mature the darker green areas of the lamina appear to have a slightly raised and crinkled texture in contrast to the light areas of the variegation which appear sunken and slightly distorted.

Inflorescence/Reproductive organ description:

Flowers and fruit of '4tune8one' appear in early summer and continue through to early autumn. The flowers are 0.59 inch to 0.83 inch wide with numerous, between 60 and 90 conspicuous stamens (as shown in FIG. 1) that are 0.51 inch to 0.83 inches long and have a whitish color of RHS 155D. The flower has a single pistil which is 0.06 inches long and is centrally located on the receptacle. The flower has four petals which are 0.16 inch to 0.24 inch long free and spreading. The lower and upper surfaces of the petals have a smooth texture; they have an entire margin and have a whitish color of RHS 155D. The petals apex and base are both obtuse in shape. The flower has four sepals with apices of an obtuse shape which are initially RHS 141D in color and change to RHS 48C with age to a final mature color of RHS 53C, this coloration occurs on the upper and lower surface of the sepals (as shown in FIG. 1). The average size of the sepals is 0.13 inches long and 0.18 inches wide, with entire margins and a smooth texture on the upper and lower surfaces. The inferior flowers appear in small clusters/panicles of 3 to 5 flowers with pedicels up to 0.39 inch long. The pedicel has a smooth surface texture and has a green color of RHS 144B. The hypanthium is campanulate in shape and 0.2 inch long. The peduncle has an average length of 0.61 inches long, has a smooth surface texture and has a green color of RHS 146B. The flowers appear throughout the foliage of the plant towards the ends of branches giving a showy appearance. The flowers have an average life of 3 to 4 days after blooming and don't have any discernible fragrance or perfume. The fruits that form are fleshy and single seeded and are obovoid in shape, 0.59 inch to 0.98 inch long by 0.31 inch to 0.79 inch wide that range in color from dark pink RHS 55A, deep pink RHS 54A and red RHS 53A. The fruits have persistent sepals and the surface texture of the fruit is smooth and silky with some minute dimpling. The edible fruits ripen through autumn to winter.

Winter growth of '4tune8one' is comparable with other *Syzygium australe* and *Syzygium paniculatum.*

The environmental temperature ranges the '4tune8one' can tolerate range from 32 degrees Fahrenheit to 104 Degrees Fahrenheit.

Disease/Drought resistance description:

Under conditions of limited water availability the new variety revives quickly on the application of water.

In general, '4tune8one' has been observed to be no more susceptible to pests and diseases than other commercial varieties.

It is claimed:

1. A new and distinct variety of *Syzygium australe* plant, substantially as shown and described.

* * * * *